(12) United States Patent
Whitten et al.

(10) Patent No.: US 11,291,835 B2
(45) Date of Patent: Apr. 5, 2022

(54) VENOM DESENSITIZER

(71) Applicants: Wesley Adolph Whitten, Arlington, TX (US); Crystal Whitten, Arlington, TX (US); Stanley Donald Abrams, Keene, TX (US)

(72) Inventors: Wesley Adolph Whitten, Arlington, TX (US); Crystal Whitten, Arlington, TX (US); Stanley Donald Abrams, Keene, TX (US)

(73) Assignee: Crystal Whitten, McDonald, TN (US)

( * ) Notice: Subject to any disclaimer, the term of this patent is extended or adjusted under 35 U.S.C. 154(b) by 44 days.

(21) Appl. No.: 16/551,048

(22) Filed: Aug. 26, 2019

(65) Prior Publication Data
US 2021/0060332 A1 Mar. 4, 2021

(51) Int. Cl.
*A61N 1/20* (2006.01)
*A61N 1/04* (2006.01)

(52) U.S. Cl.
CPC ........... *A61N 1/205* (2013.01); *A61N 1/0464* (2013.01); *A61N 1/0468* (2013.01)

(58) Field of Classification Search
CPC ..... A01M 25/00; A61N 1/205; A61N 1/0464; A61N 1/0468
See application file for complete search history.

(56) References Cited

U.S. PATENT DOCUMENTS

| | | | | |
|---|---|---|---|---|
| 3,917,268 A * | 11/1975 | Tingey | ............ | F41B 15/04 463/47.3 |
| 4,080,448 A * | 3/1978 | Mirsky | ............ | A61K 31/57 514/171 |
| 4,162,515 A * | 7/1979 | Henderson | .......... | F41H 13/0018 231/7 |
| 4,167,036 A * | 9/1979 | Kenney | ............ | F41B 15/04 231/7 |
| 4,553,748 A * | 11/1985 | Allen | ............ | A63F 9/24 463/30 |
| 4,667,431 A * | 5/1987 | Mendicino | ............ | A01K 79/02 43/6 |
| 4,873,609 A * | 10/1989 | Mackey | ............ | A61N 1/326 361/232 |
| 5,385,530 A * | 1/1995 | Wu | ............ | A61N 1/0408 601/15 |
| 2008/0132969 A1* | 6/2008 | Bennett | ............ | A61N 1/36017 607/41 |

* cited by examiner

*Primary Examiner* — Michael W Kahelin

(57) ABSTRACT

An apparatus for treating venomous bites and stings of poisonous snakes, insects and other types of poisonous vectors with a titrated dose of electrons. The unit is small and easily portable and requires on a 9-vold DC battery for power. It does not require a lot of expertise to use. A bi-metallic switch provides for a limited (and calculated) dose delivery of electrons. The venom desensitizer destabilizes and de-organizes toxic metalloproteinases. This occurs through several physiological and chemical phenomena. It addresses oxidative stress occurring from bite trauma as well as venom toxins without causing negative side effects other than a brief electrical shock.

4 Claims, 5 Drawing Sheets

Circuitry Block Diagram

Circuitry

Location Of Components

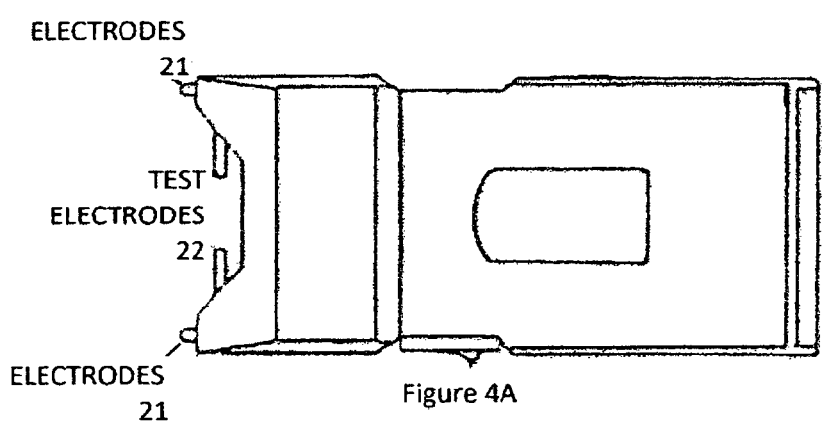
Figure 4A
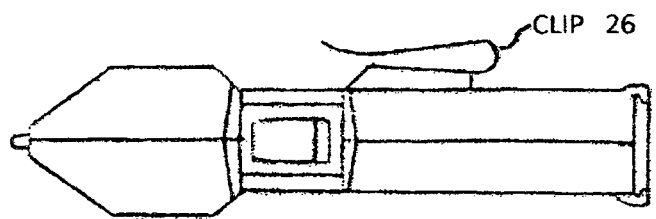
Figure 4B
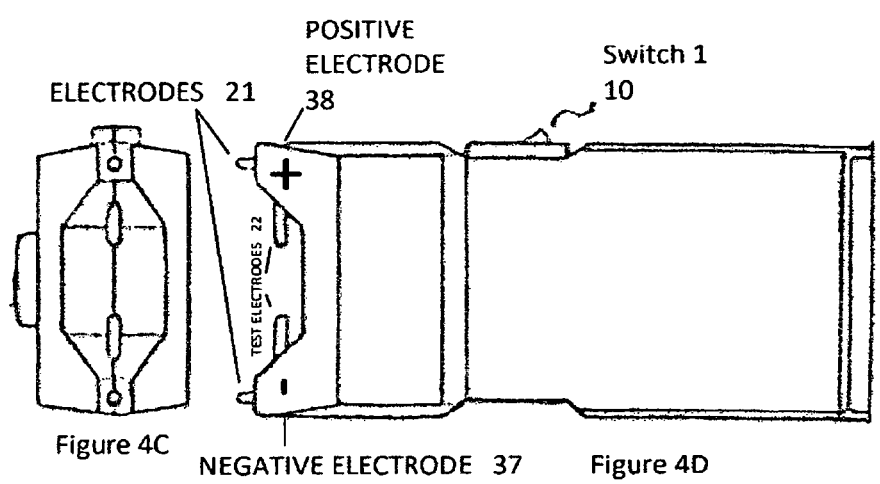
Figure 4C  Figure 4D
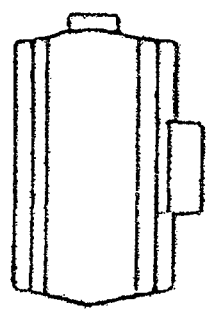
Figure 4E
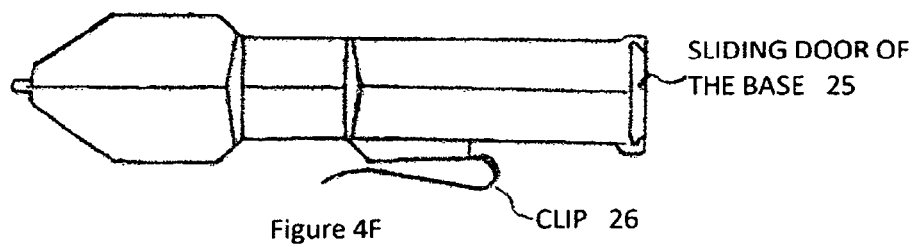
Figure 4F
Figures 4A – 4F

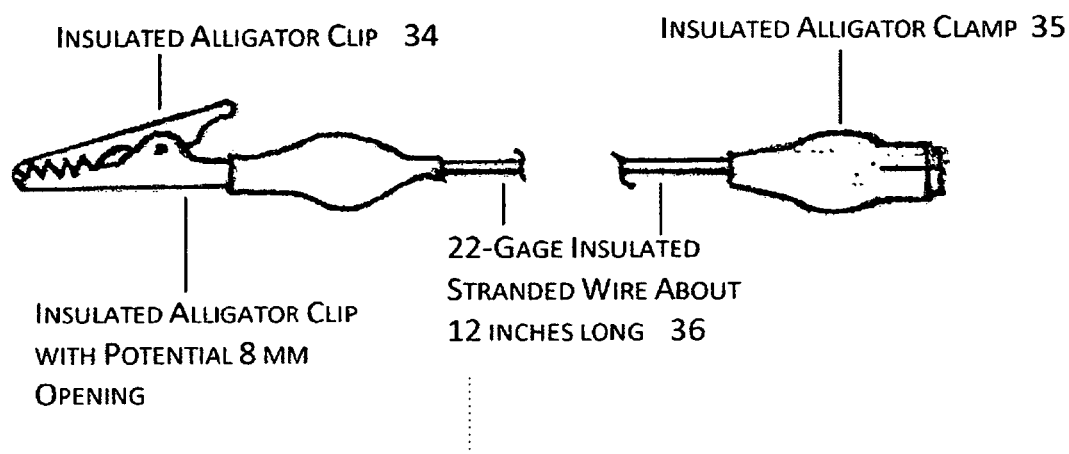
FIG 5 EXTENSION WIRE 24
INSULATED ALLIGATOR CLIP 34
INSULATED ALLIGATOR CLAMP 35
INSULATED ALLIGATOR CLIP WITH POTENTIAL 8 MM OPENING
22-GAGE INSULATED STRANDED WIRE ABOUT 12 INCHES LONG 36

VENOM DESENSITIZER

BACKGROUND

The invention is a portable, hand-held, venom desensitizer capable of generating a brief titrated dose of DC high voltage, low amperage current delivered to human tissue. It is an electronic circuit (FIG. 1 and FIG. 2) used for the treatment of venomous bites and stings. A 9-volt battery provides power to the circuit so the electrodes deliver the low amperage current through the venom-affected area, using an extension wire (FIG. 5) when necessary. This neutralizes the poisonous venom and targets the oxidative stress related to the envenomation. FIG. 3, shows the location of the components in the case (FIG. 4).

Envenomations are a traumatic and potentially life altering event. No one expects or can truly anticipate the physical repercussions, the emotional burden of both the bite or sting, the subsequent morbidity, and the financial burden a venomous bite or sting may cause. Annual U.S. and worldwide human and animal envenomations are too numerous to accurately document. Annual worldwide deaths due to envenomations is approximately 125,000, although realistically, this number is higher.

Country living and time spent outdoors increases the probability of being bitten or stung (i.e., or otherwise exposed) by a snake, spider, bee, wasp, scorpion, jellyfish, poisonous snail, poisonous frog, fire ants, etc. Farmers, agricultural workers, field biologists, pastoralists, those handling potentially venomous species, forest workers, landscapers, gardeners, hunters, fishermen, grounds keepers, construction workers, hikers, nomadic communities, campers, herdsmen, and anyone spending time outside experiences greater exposure and thus greater risk. In poor rural communities, poor sanitation, poorly constructed houses, sleeping on the floor, outdoor toilets and outdoor bathing areas increase exposure and risk. Adding to poisonous envenomations are those who are allergic to a specific species' venom, such as those with a bee sting allergy. A bite or sting may result in a minor irritation, involve significant medical interventions and/or it may cause death.

When it comes to snakebites, the majority of bite victims are between 10 and 30 years of age, typically those who spend the most time outdoors. Outside of the USA, snakebites disproportionately affect the lower socioeconomic working class. In the US, death from bites and stings is rare because of proximity to healthcare professionals and targeted availability of anti-venoms. Complications may include loss of part or all of an appendage, loss of function, permanent disability, etc. In the USA, disability due to rattlesnake bites is between 10% to 44% of those envenomated.

The morbidity of a bite is related to several aspects of both the vector and the victim. Not all snakebites envenomate their victim but the actual bite may transfer toxic pathogens (collected "data" show that around 20% to 45% are actually envenomated at the time of the snakebite). However, most people, when bitten by a snake develop signs such as rapid breathing, vasovagal shock, physical collapse, hypertension, rapid pulse, sweating, trembling, etc. Sometimes, treatments such as tourniquets, herbal remedies, incisions, cauterization, immersion in scalding liquids result in additional injuries.

Poisonous snake bites are more problematic around the world compared to the USA, although accurate worldwide data on snake, insect and other types of envenomations is difficult to ascertain. Envenomations are not a reportable event and thus, many go undocumented. Poisonous snakes bite around 1.2 to 5.5 million people per year. Scorpions sting 1.2 million people leading to 3,250 deaths per year (death rate less than 1%), but the pain associated with a scorpion bite can be so extreme it can be temporarily disabling. Spider bites, while not causing high mortality, may cause significant morbidity and lead to long-term disability.

The Global Snakebite Initiative (an international non-profit organization registered in Australia) seeks to mobilize resources to treat poisonous bites in tropical regions, particularly in the tropical areas of Africa, Asia, Latin America and parts of Oceana. Envenomations are considered to be an increasingly major and neglected tropical disease.

Efforts spearheaded by the World Health Organization (WHO) and various partner agencies targeting poisonous bites have historically fallen short of their stated objectives. In 2017 and thanks in part to the work of Dr. David Williams, the WHO placed snakebites on its top 20 priority list as a Category A Neglected Tropical Disease (for the second time).

Even with a push from the medical community to return snakebites to the WHO top 20 priority list and pockets of ongoing research, there is currently no coordinated strategy to address this pressing problem. Those not mortally bitten, live and suffer disabilities, financial devastation, psychological distress and social stigmas. Some have reported for every person who dies from a snakebite, there are another three to four people who experience major disability and are unable to return to work. To compound the issue, pharmaceutical companies have been reluctant to engage in drug formulation efforts because of historically low returns on investment, antivenom is a one-time use and not a recurring prescription, supplies are limited, and the result of major side effects of administering antivenom.

Venom from poisonous snakes and other vectors is transferred to humans via skin puncture, bite, touching, or spitting. Immediately following envenomation, redness, swelling and severe pain occur at the site and spread outward. Venom entering the systemic circulation may cause nausea, vomiting, shaking, changes in breathing, internal bleeding, kidney failure, anaphylaxis, necrotic tissue, and may require amputation and in some cases, cause death.

Sometimes venomous bites are treated by making two crosswise cuts across the puncture wound(s) and using some form of suction to physically remove the venom from the wound site. Oftentimes, out of necessity, this procedure of cutting open the skin and subsequently suctioning out toxic, poisonous venom is oftentimes done by non-medical personnel in the field, near or at the location of the envenomation. Cutting open the wound and suctioning out venom is risky, especially when done by a non-medical person. The possibility of cutting an artery, nerve or cutting deeper and broader may cause the victim to go into shock and die from blood loss. It is possible to introduce foreign pathogens or other matter to the wound cut area and this may lead to infection and activation of pyrogenic factors, also increasing the likelihood the victim will die before reaching appropriate medical professionals. There is also a chance of blood poisoning if the suction does not remove all or most of the venom. The person performing the cutting procedure may also be at risk. Currently the Red Cross does not recommend this treatment.

Limited numbers of pharmaceutical companies engage in antivenom production. Vectors vary in their individual venom profiles (even within the same species) making antivenom, to some degree, less effective. "Specific" antivenom implies the antivenom has been created using the actual venom vector. Monovalent antivenom (monospecific) neutralizes the venom of only one species of snake. Polyvalent antivenom neutralizes the venom of several different snake species. Antivenom safety is a legitimate concern. Reports suggest 6% to 59% of those treated with antivenom experience early onset reactions from the administration of animal-based plasma-derived antivenoms. Another 5% to 23% of anti-venom treated victims experience delayed onset serum sickness (typically observed one to two weeks after antivenom treatment). Highly purified antivenoms, primarily available in or near hubs of modern medicine, have much lower rates of early adverse reactions. Administration of antivenom may be associated with side effects such as flushing, itching hives, face/tongue/throat swelling, cough, shortness of breath, cyanosis, vomiting and anaphylaxis. Very close medical supervision is required when administering antivenom.

Dr. Robert Harrison, Director of the Alistair Reid Venom Research Unit, is spearheading scientific research to improve the quality of antivenoms and ultimately develop a universal antivenom for sub-Saharan Africa. The lack of robust engagement by the pharmaceutical industry in the development and manufacture of antivenoms will likely continue, thus making the need for alternative treatments, even with variable efficacy, important. In addition, most currently marketed antivenoms have never been formally tested for safety and efficacy. Ideally it is best to match snakebite antivenom to the actual vector, but this rarely occurs. In fact, most times the bite vector species is not positively identified. Most antivenoms do not address tissue destruction (i.e., necrosis) caused by specific toxins.

Each poisonous bite potentially represents an existential threat. For example, most people will not die when stung by a bee unless they have had multiple stings. Most people will not die from an intensely painful jelly fish sting unless you are stung by a box jelly fish. In these cases, one only has a matter of seconds, maybe minutes before dying from highly toxic venom. In the USA, the Arizona bark scorpion carries the most toxic venom, but relatively few deaths are associated with its extremely painful and distressing bite. If you are stung by the South Indian *Mesobuthus tamulus* scorpion (i.e., found in India, eastern Pakistan, the lowlands of Nepal, and Sri Lanka), your body may go into an "autonomic storm" and the risk of life-threatening cardiogenic shock is significant. Even if you reach medical personnel, you may be at long term risk for cardiac-related pathophysiology.

Venom based toxicology has identified numerous compounds that vary in biological activity and toxicokinetic profiles. Each vector and its consort of toxins transferred to the victim's body results in variable pathology. In fact, it may be difficult to predict the effects due to our limited understanding of how a multiple toxin cocktail impacts human biology. Kroegel, et al., states there are at least 26 enzymes found in snake venoms and 12 are found in all venoms including the venom melittin, which stimulates phospholipase A and hyaluronidase, causing pain and inflammation at the site of envenomation. Additional toxins are various proteins and polypeptides, characterized by an overall net positive charge (e.g., cardiotoxin cytotoxin and direct lytic factor). The venom proteins and polypeptides potentiate the actions of phosphoslipase A. Some toxins are low molecular mass proteins and circulate throughout the body, easily accessing the peripheral nervous system. Higher molecular mass toxins such as metallo- and serine proteinases while accessing the systemic circulation, are found at a lower volume due to their larger molecular size. They are associated with hemorrhage and coagulation disorders.

In an editorial interview by Chao Xiao of venom researchers, Jay Fox and José Maria Gutierréz and published in Toxins (2017), Jay Fox provides the following guidance in understanding toxic venoms. They are listed in the order provided:

(a) Venoms are comprised of toxic and non-toxic components (many of which are proteins and peptides).
(b) In many venoms, the activity of toxins is dependent on enzymatic activities directed at specific substrates.
(c) In the case of snake venom metalloproteinases (SVMPs), the hemorrhagic SVMPs were demonstrated to disrupt the basement membranes of capillaries allowing the extravasation of contents into the stroma.
(d) Venoms are somewhat complex and this is demonstrated by proteomics and transcriptomics.
(e) The toxic effects of venom are due to the collective action of toxins and non-toxic components in the venom and to understand envenomation, must ultimately take a systems approach.
(f) Development of anti-venom agents must always consider the venom as a system; not a simple collection of unilaterally acting toxins.
(g) By discovering the activities of toxins we will better understand the function and structure of normal orthologs, and by understanding the targets and the nature of the toxin mechanisms, the possibility of developing novel drugs becomes a reality.

In the same editorial interview by Chao Xiao, interviewee Jose Maria Gutierréz, went on to state the study of venomous toxins would merge with the study of promising new drugs for treating a variety of diseases. While medical researchers make promises about future antivenoms, we have a solution that addresses the major actions of the venom when administered in easily titrated doses. This method has been successfully used by numerous physicians in the treatment of poisonous snake bites, brown recluse spider bites, fire ant bites and others. In treating somewhere between 300 to 400 cases of poisonous bites, Dr. Stan Abrams has only bad a single failure using a similar device. The one failure was in an obese person, where excess abdominal fat, acting as an insulator, interfered with the delivery of high voltage DC electrons. This method has not only addressed envenomations, but has reversed the ongoing and disabling effects of a brown recluse spider bite, 1.0 years after the initial envenomation. Other physicians and medical personnel known to this team of investigators/inventors have treated multiple hundreds of clients with outstanding success. A previous version of this unit has been successfully used by veterinarians to treat snake-bitten dogs.

Brown recluse spider venom contains a necrotizing type venom, known to target and damage local as well as systemic tissue, including damage to the kidneys. Ideally, toxin neutralization is timely, systemic, and targets both low and high molecular mass metalloproteinases and serine proteinases. From an antigenic perspective, toxins are considered to be neutralized when they are bound by the variable region of an antibody. In addition to neutralizing the toxin-based metallo- and serine proteinases there may be other novel avenues of neutralizing toxins such as changing protein structures and slowing or halting damaging oxidative type reactions. Ultimately, all toxins, but especially necrotizing toxins cause massive oxidative damage to local tissues. The oxidative damage almost always overwhelms the body's cytological immune responses. As long as the toxin is in its active form, it causes local as well as potentially systemic effects. Delivery of a dosed and titrated electric shock to human tissue possessing electro-magnetic properties, forces a biological correction that antivenoms are not currently able to imitate. The correction involves a structural alteration in the venom molecule that is rapid and in almost all cases leads to a successful resolution.

The actions of the venom desensitizer may also overlap plant-based folk remedies. For centuries, natural remedies such as plants have been applied to toxic bites and stings with minimal success. Patino A. C., et al., describe how the plant *Renealmia alpina*, has been used to neutralize edema-forming, hemorrhagic, lethal and fibrin(ogen)ating actions of Bothrops asper venom. The plant is described as inhibiting the enzymatic and toxic activities of snake venom metalloproteinase (inhibition of proteolytic activity on fibrinogen), inhibiting serine proteinase activity, inhibiting coagulant, and inhibiting edema-causing properties of venom. In addition to the plant *Renealmia alpina*, more than 700 plants have experimentally demonstrated various degrees of venom neutralizing properties. The compounds thought to neutralize the venom components act in various mechanistic modes including high doses of free electrons acting as antioxidants and altering pH, slowing or halting oxidative reactions, and changing metal binding affinities of venom metalloproteinases. It is possible the transfer of electrons also modifies or causes metabolic enhancements that rapidly neutralize toxins. The venom desensitizer is a novel way to safely and efficiently deliver and titrate large millisecond doses of electrons, transdermally. This unit allows the operator to rapidly address potentially venomous and toxic encounters with the most healing, least damaging option of high voltage electron transfer. This method alone or when combined with additional therapies begins to immediately stop the toxic actions of the venom. In addition, the high voltage donation/transfer of electrons provides a large dose of antioxidants to stop progressive oxidative reactions. In contrast, the use of pharmaceutical antivenoms transfer foreign, "unrecognizable," and allergenic proteins in the form of horse-based globins to humans. It is normal to expect rejection reactions, which occur and can be medically serious. In contrast, when external high dose electrons (i.e., which are the same as those already in the body), are delivered to the body via high voltage and low amperage, outstanding results are reported with no reported untoward side effects.

The venom desensitizer is a battery driven electronic unit for transmitting high DC voltage and low amperage energy to the envenomation site. This destabilizes and de-organizes toxic metalloproteinases. This occurs through several physical and chemical phenomena including electrolysis (inducing a non-spontaneous chemical reaction) and electrophoresis. It also ends oxidative reactions by providing large amounts of free electrons without causing negative side effects other than a brief electrical shock.

In summary, an earlier version of this product has been used for several decades by a few physicians who became familiar with this technology and its unique application in treating venomous bites. However, previous versions of this product (which was referred to as stun gun) have come under legal scrutiny and restrictions on sales have been imposed in a number of states. Currently, each state determines whether or not stun guns are regulated; in some states, one must be a weapons dealer to sell a stun gun. To circumvent this issue, the device described in claims 1 (currently amended) and 2 (currently amended) of this patent application is configured to only activate one or two cycles (i.e., one zap) per activation of the switch, and not be continuous. Previous designs delivered 12 cycles (i.e., zaps) per second and would remain "on" as long as the switch was activated. In summary the device described in claims 1 (currently amended) and 2 (currently amended) of this patent application differs significantly from previous designs in the following two ways: first, as previously described here, it is both in design and function, limited to one or two discharges for each press of the activating switch. This is a significant and highly targeted difference between the device described in claims 1 (currently amended) and 2 (currently amended) of this patent application and a significant departure from the Mackey patent (U.S. Pat. No. 4,873,609). It is not an open switch and prevents the use of this device as a personal safety or criminal deterrent unit. Stun guns and even the device described in claim 1 (currently amended) is similar to other DC driven devices such as electronic dog collars, electric fences, etc. This unit described in claims 1 (currently amended) and 2 (currently amended) of this application, is simple and straightforward and may be used, even by a child of 12+ years of age. There is low risk associated with its use. The pain associated with using this unit, while ranking fairly high on the pain scale, is brief and short-lasting, an absolutely acceptable trade-off for stopping pathological processes associated with most poisonous envenomations.

Even though a previous version of this unit has historically been highly effective in treating and resolving poisonous envenomations, this unit is not intended to confer a false sense of security. Non-venom issues such as bacterial infections, psychological and others issues should motivate those spending significant time outdoors to use caution and care in avoiding encounters with venomous vectors. This unit excels in the ability to titrate delivery of single doses of DC electrons.

In summary, the efforts of hundreds of researchers studying venoms and their actions for wide-ranging applications is indicative of a reductionist view, the view that pharmaceutical drugs are the solution to almost all human pathological phenomena. The search for non-drug solutions would more likely lead to "natural" or even a forced type of "biological correction." This type of successful biological correction could be further augmented by diet and lifestyle choices as well as mild pharmaceutical adjuncts but they are not necessary for successful resolution of bites and stings treated by this unit.

The venom desensitizer covers a wide range of venom types. It does not require a professional to administer. There is very low risk associated with its use. The cost of this unit is extremely small compared to securing standard-of-care medical interventions that may cost hundreds of thousands of dollars and span weeks to decades. High voltage and low amperage are associated with enough current to override skin resistance and penetrate through the envenomated tissue without harming soft tissue or bone. The dose of electrons delivered to the bite area aids in stopping the oxidative stress associated with toxins as well as promoting rapid healing. High voltage and low amperage associated with each single titrated shock will alter venom proteins and change valence of metallic ions on the enzymes of most venoms, inactivating the toxin and allowing the body's innate detoxification functions to eliminate the neutralized toxin.

REFERENCES CITED

2. Bawaskar, H S, & Bawaskar, P H (2011). Efficacy and safety of scorpion antivenom plus prazosin compared with prazosin alone for venomous scorpion (*Mesobuthus*

*tamulus*) sting: randomised open label clinical trial. BM (Clinical research ed), 342, c7136. doi:10.1136/bmj.c7136.
3. Williams D J, Habib A G, Warrell D A. Clinical studies of the effectiveness and safety of antivenoms. Toxicon 2018 150:1-10.
4. Ulrik Birgersson (Stockholm 2012). Electrical impedance of human skin and tissue alterations: mathematical modeling and measurements. Dept Clinical Science, Intervention and Technology Karolinska Institutet, Stockholm, Sweden.
5. Foster K R, Schwan H P. Dielectric-Properties of Tissues and Biological Materials—a Critical Review. Critical Reviews in Biomedical Engineering vol. 17, pp 25-104, 1989.
6. Gabriel S, Lau R W and Gabriel C. The dielectric properties of biological tissue: 11. Measurements in the frequency range 10 Hz to 20 GHz. Phys. Med. Biol. 1996; 41: 2251-69.
7. Iwai I, Han H, den Hollander L, Svensson S, Öfverstedt L, Anwar J, Brewer J, Bloksgaard M, Laloeuf A, Nosek D, et al. The human skin barrier is organized as stacked bilayers of fully extended ceramides with cholesterol molecules associated with the ceramide sphingoid moiety. Journal of Investigative Dermatology 2012; 132: 2215-2225.
8. Curing the Incurable: Vitamin C, Infectious Diseases and Toxins, $3^{rd}$ ed, by Thomas Levy. Medfox Publishing (1 Aug. 2011). ISBN-13: 978-0977952021.
9. Clinical Guide to the Use of Vitamin C: The Clinical Experiences of Frederick R. Klenner, M D (1988) by Lendon Smith, Life Sciences Press (1 Oct. 1991). ISBN-13: 978-0943685137
10. Patino A C, Benjumea D, and Pereanez A. Inhibition of venom serine proteinase and metalloproteinase activities by *Renealmia alpinia* (Zingiberaceae) extracts: comparison of wild and in vitro propagated plants. J. Ethnopharmacology, 149(2), August 2013.
11. Editorial. Snake-bite envenoming: a priority neglected tropical disease. Lancet, 1 Jul. 2017, 390; 10089, p 2.

SUMMARY OF INVENTION

Portable DC unit for delivery of a single titratable dose of free electrons at the site of envenomation in the treatment of venomous bites, allergic reactions to insect stings and other animals and contact with poisonous plants and their toxins. An extension wire provides a means of ensuring adequate coverage of large affected areas of the bite/sting area. The medical application of high voltage DC electrons in the treatment of venomous bites has been described by Ronald H. Guderian, Charles D. Mackenzie and Jeffrey F. Williams in the journal, Lancet (High Voltage Shock Treatment for Snake Bite, Lancet, 26 Jul. 1986). A follow-up publication in the same journal (Kroegel C, Meyer K H and Buschenfelde Z, Biological Basis for High-voltage-shock treatment for snakebite, Lancet, 6 Dec. 1986), provides additional details. Venomous vectors are primarily found in the wild but in the cases of venomous spiders and scorpions, the vectors may invade and occupy buildings and living spaces. When planning to spend time outdoors, most people consciously assume a degree of risk related to venomous vectors, caustic plants, and flying and stinging insects (i.e., although combining alcohol and drugs with outdoor activities oftentimes leads to poor judgment and increased risky behaviors). Even inadvertent contact with fire ants can be acutely and excruciatingly painful. The pain may be brief or it may last for days with significant local and even systemic effects. When humans invade nature's space and nature invades our living spaces, the effects can be nothing short of traumatic. If there was an effective and efficient tool or method to treat venomous bites and stings, it would significantly impact how most of the world lives and views the risk associated with venomous bites. If the tool or treatment was highly effective, it could truly change the nature of outdoor activities, including farming, agriculture, outdoor professions, camping, hiking, etc. The present invention utilizes several unique aspects of high voltage DC current directed to the envenomation site to neutralize the venom. For the above scenarios, the use of a high voltage and low amperage DC electrical device to neutralize the venom, disassociate the venomous components and slow down or halt the oxidative stress, is a desirable option for those working outdoors, in the agricultural sector, ranchers, hikers, campers, water sports, veterinarians, etc. The transfer of approximately 18 Kv to 25 Kv, at a distance of 50 mm between the contact electrodes (or longer distances when the extension wire is needed), overcomes skin resistance and delivers a direct current shock to the envenomation site, effectively stopping the venom's action. High voltage transfer of electricity to envenomated biological tissue leads to early pain relief and diminished local toxic and inflammatory tissue reactions and jump-starts healing and recovery reactions. Most bites require at least four and possibly five zaps (with some zaps utilizing an extending ground wire contacting the back side of the bite limb or extremity) with approximately 18 Kv to 25 Kv per zap. Electrons quickly attack the oxidative actions of venom and at high doses, rapidly take over the restoration of normal functions. To approximate the number of electrons delivered by a $\frac{1}{12}^{th}$ of a second zap at 0.1 amp using Coulomb's equation, is equivalent to $6 \times 10^{16}$ electrons. Additional adjunctive oral and/or intravenous therapies using vitamin C and/or glutathione would support DC delivered electron therapy.

BRIEF DESCRIPTION OF THE DRAWINGS

FIG. 4A is a view of the backside (prone view)

FIG. 4B is a view of the right or the switch 10 or the positive electrode side

FIG. 4C is a view of the top (supine view)

FIG. 4D is a view of the front side

FIG. 4E is a view of the bottom side

FIG. 4F is a view of the left or negative electrode side

FIG. 5 is a view of the extension wire which includes an insulated alligator clip on one end of the 22-gage insulated stranded wire about 12 inches long and an insulated alligator clamp on the other end

DETAILED DESCRIPTION

Figure 1:
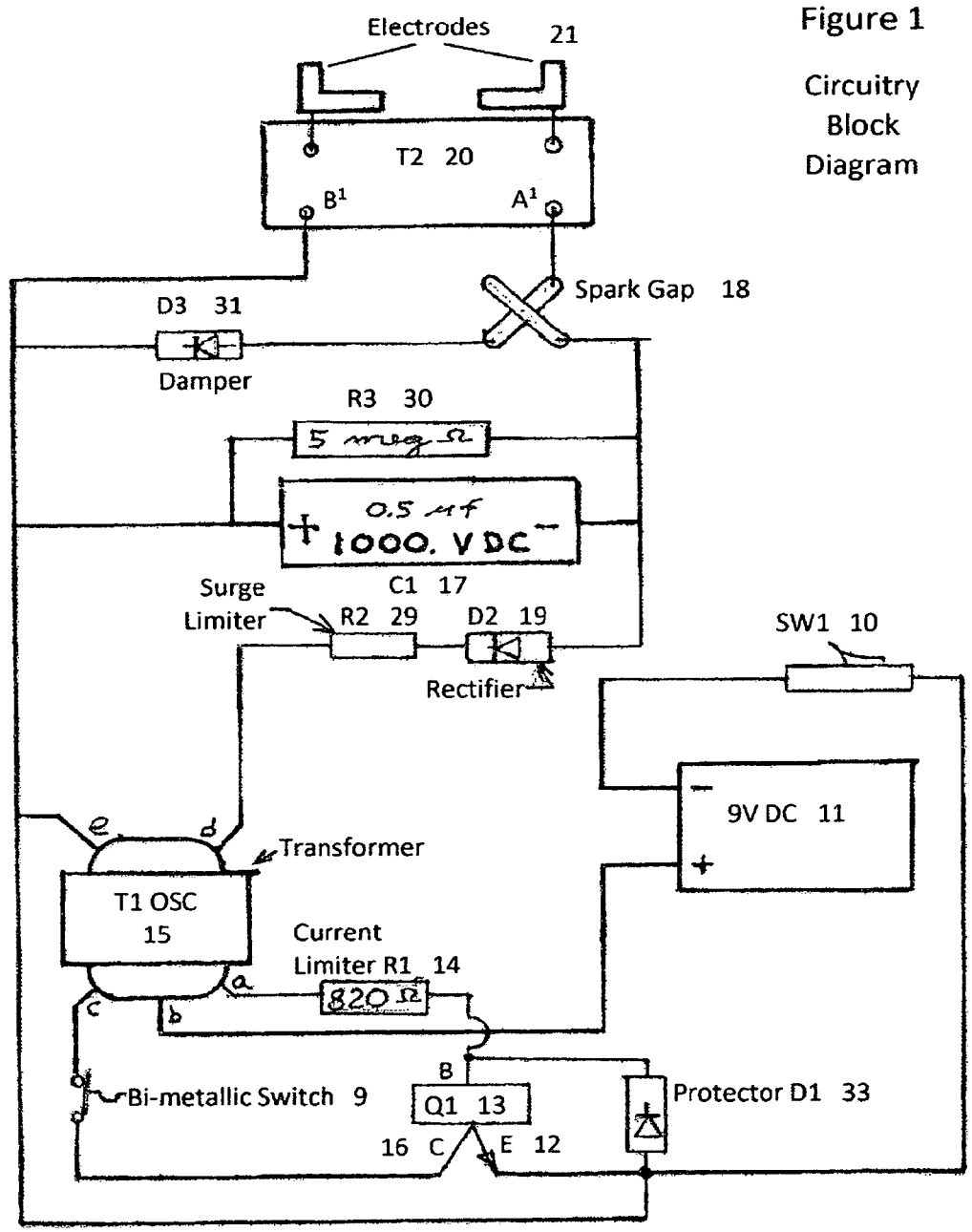
FIG. 1 Illustrates in block diagram form the circuitry required to produce the current across the DC electrodes 21
Figure 2:
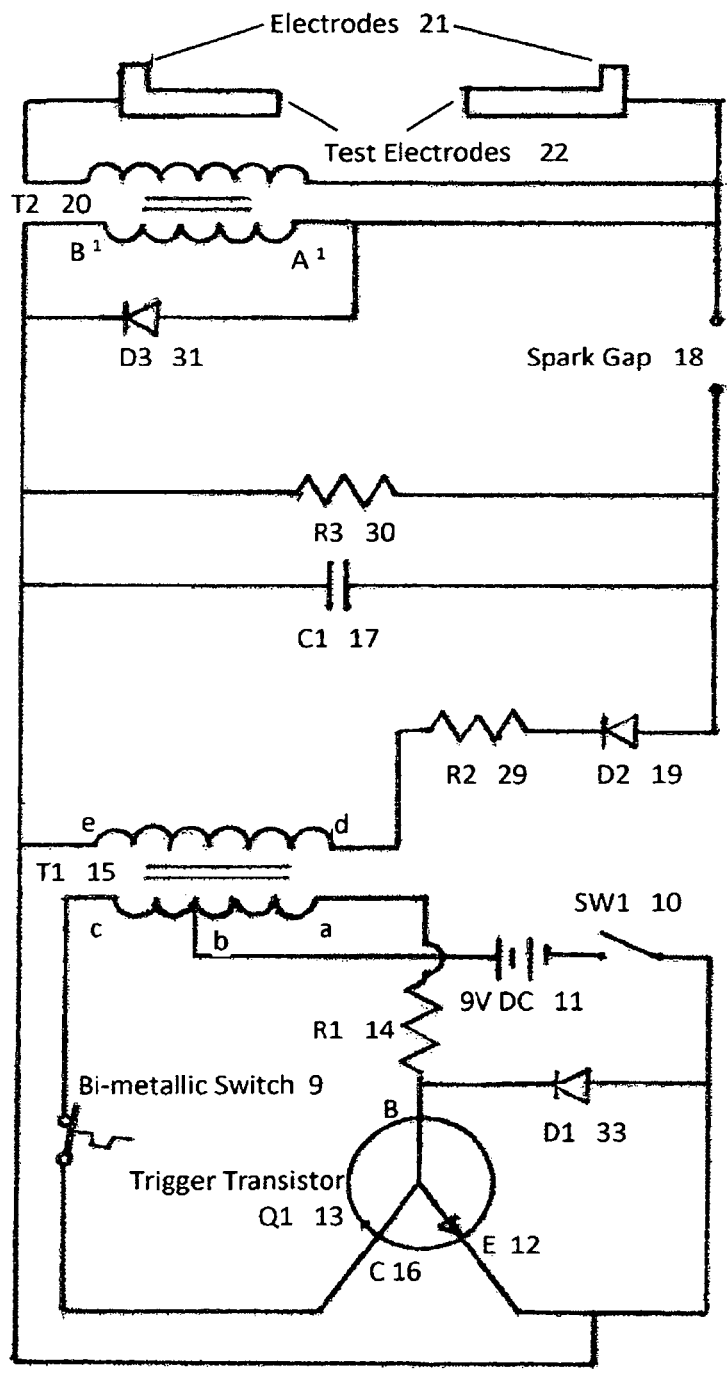
FIG. 2 Illustrates the circuitry to produce the desired DC current across the electrodes 21 and shows the resistors (14, 29, 30), transformers (15, 20), the spark gap 18, diodes (19, 31, 33), the capacitor (17), the trigger transistor 13, and the voltage of the power source 11

Referring to the drawings numbered, 1, 2, 3, 4A, 4B, 4C, 4D, 4E, 4F, and 5. The progressive operation of the circuit is:

FIGS. 1 and 2 show when SW1 10 is closed current flows from battery 11 through SW1 10 in the emitter base 12 of Q1 13 through R1 14 (820 ohms), then a*b of transformer T1 15 to plus terminal of the battery 11. This action turns on Q1 13, collector current flows from the minus terminal of the battery 11 to emitter 12 to collector 16, through a bi-metallic switch or a momentary "on" switch 9, to c*b of transformer T1 15 to plus of battery 11. This increasing current causes a magnetic field buildup about T1 15 inducing positive or regenerate voltage across E/B junction of Q1 13 thus driving the transistor 15 into saturation. Due to no further change in current, the magnetic field collapses, inducing a reverse voltage across E/B driving Q1 13 into cut off.

As shown in FIGS. 1 and 2, the oscillator circuit continues at a rate of approximately 12 KHZ (12,000 Hz). Approximately 1,000 pulses charges C1 17. T1 15 is also a step-up transformer. These pulses are induced across d*e of transformer T1 15. Then flows through R2 29, then through D2 19 then charges C1 17. When approximately 1,000 volts are across C1 17, the spark gap 18 discharges C1 17 through primary T2 19 (A' to B') R3 30 slowly discharges C1 17. This action induces approximately 25 Kv pulse across step up transformer T2 20 to the electrodes 21. This DC pulse appears across electrodes 21. The distance between the test electrodes 22 is 15 mm and the distance between the contact electrodes 21 is 50 mm.

Figure 3:
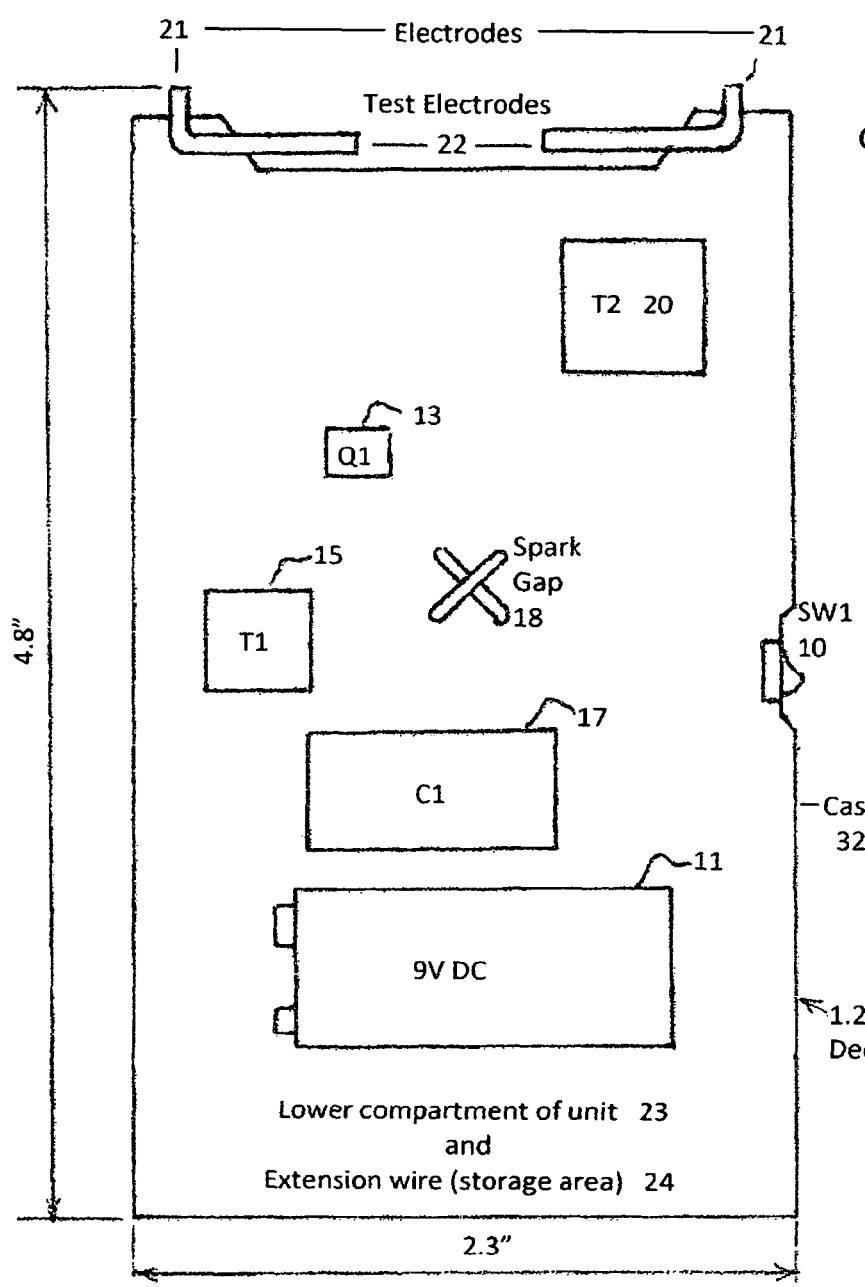
FIG. 3 Illustrates the size, dimensions, and positioning of the various electronic components in a carrying case 32

FIG. 3 shows the location of the components; a 9 volt battery 11 transformers T1 15 and T2 20 spark gap 18 damper D3 31 switch 1 (SW1) 10 the capacitor (C1) 17 the Q1 transistor 13 the electrodes 21 and the lower compartment 23 for storing the extension wire 24.

FIGS. 4A, 4B, 4C, 4D, 4E, and 4F show the external casing 32 for the electrical mechanism. FIG. 4B, is an external view of the switch 10. FIG. 4C shows a top view of the electrodes 21 and 22. It is enclosed in a plastic case 32 with a sliding door 25 at the base of the unit (see FIGS. 4D, 4E and 4F) for inserting the 9-volt battery 11 and the extension wire 24. This case 32 has a clip 26 on the back side for clipping this unit to a belt, etc. (see FIG. 4A).

FIG. 5 shows the extension wire 24 with an alligator clip 34 on one end of a stranded wire 36 with an alligator clamp 35 on the other end. The alligator clip attaches to the negative electrode 37 of the unit, with current extending to the insulated alligator clamp end 35, which is placed against the skin. Current travels from the alligator clamp 35 through biological tissue to the positive electrode 38.

While the invention has been described with a certain degree of particularity, it is manifest that many changes may be made in the details of construction and the arrangement of components without departing from the spirit and scope of this disclosure. It is understood that the invention is not limited to the embodiments set forth herein for purposes of exemplification, but it is to be limited only by the scope of the attached claim or claims, including the full range of equivalency to which each element thereof is entitled.

This is an electronic unit providing an antidote for the treatment of venomous bites of various vectors including but not limited to the following species of fire ants, bees, jelly fish, scorpions, snails, snakes, spiders, wasps, poisonous plants, toxins, etc. The electrodes 21 are pressed to the skin around the bite area and four or five zaps are applied in a circular method at 12, 3, 6 and 9 o'clock positions with a fifth treatment using the extension wire 24 if necessary. Functionally, when using the extension wire 24, the current is released from the negative electrode 37 of the unit attached to the alligator clip 34, travels along the insulated stranded wire 36 and through the alligator clamp 35 which is touching the skin, and then current travels through biological tissue reaching the positive electrode 38.

In addition to the treatment of venomous bites and stings, the transfer of electrons to biological tissue has been shown to be useful for the treatment of symptoms related to inflammation and pain.

PARTS LIST 9 bi-metallic or momentary "on" switch 10 SW1 switch 11 9-volt DC battery 12 E-terminal on Q1 13 Q1 transistor 14 R1 resistor 15 T1 transformer 16 C terminal on Q1 17 C1 1000 volt capacitor 18 spark gap 19 D2 rectifier 20 T2 transformer 21 electrodes 22 test electrodes 23 lower compartment of unit 24 extension wire 25 sliding door on base of unit 26 clip 29 R2 resistor 30 R3 resistor 31 D3 diode 32 plastic case 33 D1 34 alligator clip 35 alligator clamp 36 22-gage insulated stranded wire 37 negative electrode 38 positive electrode

What is claimed is:

1. A portable hand-held, battery powered, venom/poison/toxin desensitizer system in a self-contained unit, with a hand-operated switch and capable of generating a DC signal of high voltage and low amperage and deliver a single or double dose in the range of milliseconds across the skin barrier of a patient and locally through living tissue exposed to a venomous and/or poisonous toxin and configured to treat bites by poisonous snakes and other vectors, other venomous animals, and/or acute pro-oxidative reactions or conditions comprising:

a battery;
an electrical circuit;
a hand-operated switch configured to connect the battery to the electrical circuit,
wherein the electrical circuit includes an automatic switch configured to produce at an output a single or double millisecond discharge at a voltage between 15 kV and 25 kV, the automatic switch ensuring only a single or double millisecond discharge per activation of the hand-operated switch;
a pair of electrodes connected to the output of the electrical circuit;
a 12-inch 22 gage extension wire with an insulated electrode on one end and a small insulated alligator clip on the other end configured to clamp to one of the pair of electrodes and configured to extend the treatment area by being attached to a remote location on the patient; and
a hand-held case containing the battery, the extension wire, the electrical circuit, and the automatic switch,
wherein the hand operated switch and the pair of electrodes reside on the outer surface of the housing, and
wherein the pair of electrodes are not greater than 50 mm apart to thereby ensure the current is not over 1 mA at either electrode.

2. A method comprising:
applying the portable hand-held, battery powered, venom/poison/toxin desensitizer system of claim 1 to a patient; and
titrating doses of electrons thereby treating specific venomous vectors using specific doses of electrons.

3. The method of claim 2, wherein titrating includes applying the portable hand-held, battery powered, venom/poison/toxin desensitizer system to the patient's tissue in a circular method at 12, 3, 6, and 9 o'clock positions.

4. The method of claim 3, further comprising applying the portable hand-held, battery powered, venom/poison/toxin desensitizer system using the extension wire if the circular method is ineffective.

\* \* \* \* \*